United States Patent
Zhang et al.

(10) Patent No.: US 12,311,031 B2
(45) Date of Patent: May 27, 2025

(54) ANTIBODIES SPECIFIC TO CD44

(71) Applicant: Multitude Inc., Shanghai (CN)

(72) Inventors: Shaofei Zhang, Shanghai (CN); Bing Hou, Shanghai (CN); Guangcun Cheng, Shanghai (CN); Shu-Hui Liu, Redwood City, CA (US); Xun Meng, Shanghai (CN)

(73) Assignee: Multitude Inc., Shanghai (CN)

( * ) Notice: Subject to any disclaimer, the term of this patent is extended or adjusted under 35 U.S.C. 154(b) by 812 days.

(21) Appl. No.: 17/386,197

(22) Filed: Jul. 27, 2021

(65) Prior Publication Data
US 2022/0049008 A1     Feb. 17, 2022

Related U.S. Application Data

(63) Continuation of application No. PCT/US2020/014425, filed on Jan. 21, 2020.

(30) Foreign Application Priority Data

Jan. 28, 2019   (WO) ................ PCT/CN2019/073402

(51) Int. Cl.
| | | |
|---|---|---|
| A61K 47/68 | (2017.01) | |
| A61K 38/00 | (2006.01) | |
| C07K 14/705 | (2006.01) | |
| C07K 14/725 | (2006.01) | |
| C07K 16/28 | (2006.01) | |
| A61K 35/00 | (2006.01) | |

(52) U.S. Cl.
CPC .... *A61K 47/6849* (2017.08); *A61K 47/68031* (2023.08); *C07K 14/7051* (2013.01); *C07K 14/70517* (2013.01); *C07K 14/70578* (2013.01); *C07K 16/2884* (2013.01); *A61K 38/00* (2013.01); *C07K 2317/24* (2013.01); *C07K 2317/34* (2013.01); *C07K 2317/565* (2013.01); *C07K 2319/02* (2013.01); *C07K 2319/03* (2013.01); *C07K 2319/30* (2013.01); *C07K 2319/33* (2013.01)

(58) Field of Classification Search
CPC ................................................ C07K 16/2884
See application file for complete search history.

(56) References Cited

U.S. PATENT DOCUMENTS

| | | |
|---|---|---|
| 2008/0171042 A1 | 7/2008 | Iczkowski et al. |
| 2012/0003227 A1 | 1/2012 | Sukhatme et al. |
| 2017/0014524 A1 | 1/2017 | Chatterjee et al. |
| 2017/0247428 A1 | 8/2017 | Bondanza et al. |

FOREIGN PATENT DOCUMENTS

| | | | | |
|---|---|---|---|---|
| CN | 101616933 A | | 12/2009 | |
| CN | 108290939 A | | 7/2018 | |
| CN | 109311995 A | | 2/2019 | |
| CN | 113896793 A | * | 1/2022 | |
| WO | WO 95/00851 A1 | | 1/1995 | |
| WO | WO-2011022335 A1 | * | 2/2011 | ............. A61P 35/00 |

OTHER PUBLICATIONS

Dall et al. "Increasing Incidence of CD44v7/8 Epitope Expression During Uterine Cervical Carcinogenesis". Int. J. Cancer (Pred. Oncol.): 69,7945 (1996) (Year: 1996).*
Dall et al. "Efficient Lysis of CD44v7/8-Presenting Target Cells by Genetically Engineered Cytotoxic T-Lymphocytes—A Model for Immunogene Therapy of Cervical Cancer". Gynecologic Oncology 66, 209-216 (1997) Article No. GO974777 (Year: 1997).*
Dall et al., In vivo cervical cancer growth inhibition by genetically engineered cytotoxic T cells. Cancer Immunol Immunother. Jan. 2005;54(1):51-60. doi: 10.1007/s00262-004-0569-x. (Year: 2005).*
Matsuzaki. "Anti-glypican-1 antibody-drug conjugate exhibits potent preclinical antitumor activity against glypican-1 positive uterinecervical cancer". International Journal of Cancer vol. 142, Issue 5, Mar. 2018, pp. 867-1078 (Year: 2018).*
Vajdos et al. "Comprehensive Functional Maps of the Antigen binding Site of an Anti-ErbB2 Antibody Obtained with Shotgun Scanning Mutagenesis". J Mol Biol. 2002; 320(2):415-428 (Year: 2002).*
International Search Report and Written Opinion for Application No. PCT/US2020/014425, mailed Jul. 20, 2020.
International Preliminary Report on Patentability for Application No. PCT/US2020/014425, mailed Aug. 12, 2021.
Ylagan et al., Cd44: a marker of squamous differentiation in adenosquamous neoplasms. Arch Pathol Lab Med. Feb. 2000;124(2):212-5. doi: 10.5858/2000-124-0212-C.
Extended European Search Report for Application No. 20747727.4, mailed Oct. 6, 2022.
No Author Listed, Datasheet: MCA1732: Mouse Anti Human CD44v7/8 VFF-17. Biorad laboratories Inc. Mar. 21, 2022. 3 pages. Retrieved from the Internet: https://www.bio-rad-antibodies.com/monoclonal/human-cd44v7-8-antibqdy-vff-17-mca1732.html?f=purified [retrieved on Sep. 21, 2022].
Wibulswas et al., The CD44v7/8 epitope as a target to restrain proliferation of fibroblast-like synoviocytes in rheumatoid arthritis. Am J Pathol. Dec. 2000;157(6):2037-44. doi: 10.1016/S0002-9440(10)64842-0.
Zoller, CD44: can a cancer-initiating cell profit from an abundantly expressed molecule? Nat Rev Cancer. Apr. 2011;11(4):254-67. doi: 10.1038/nrc3023. Epub Mar. 10, 2011.

(Continued)

*Primary Examiner* — Janet L Epps-Smith
*Assistant Examiner* — Lea S O'Brien
(74) *Attorney, Agent, or Firm* — Wolf, Greenfield & Sacks, P.C.

(57) ABSTRACT

Antibodies having binding specificity to CD44 v7/8, (a.k.a. CD44 variant 7/8) and antibody-drug conjugates (ADCs) or chimeric antigen receptors comprising such. Also provided herein are uses the anti-CD44 v7/8 antibodies, the ADCs, or immune cells expressing the chimeric antigen receptors for therapeutic and diagnostic purposes.

19 Claims, 4 Drawing Sheets
Specification includes a Sequence Listing.

(56) References Cited

OTHER PUBLICATIONS

PCT/US2020/014425, Jul. 20, 2020, International Search Report and Written Opinion.
PCT/US2020/014425, Aug. 12, 2021, International Preliminary Report on Patentability.

* cited by examiner

ANTIBODIES SPECIFIC TO CD44

RELATED APPLICATIONS

This Application is a continuation of International Patent Application No. PCT/US2020/014425, filed Jan. 21, 2020, entitled "ANTIBODIES SPECIFIC TO CD44". Foreign priority benefits are claimed under 35 U.S.C. § 119 (a)-(d) or 35 U.S.C. § 365 (b) of PCT application number PCT/CN2019/073402, filed Jan. 28, 2019. The entire contents of each of these applications are incorporated herein by reference.

BACKGROUND OF THE INVENTION

CD44, also known as HCAM (homing cell adhesion molecule), Pgp-1 (phagocytic glycoprotein-1), Hermes antigen, lymphocyte homing receptor, ECM-III, or HUTCH-1, is a cell-surface glycoprotein that functions primarily in cell adhesion and cell-cell interactions. Several splice variants of CD44 are known, including CD44 v7/8, which is a variant comprising exon 7 and exon 8. CD44 is a protein receptor for hyaluronic acid and has further been shown to bind or otherwise interact with osteopontin, collagens, matrix metalloproteinases, and other similar ligands.

SUMMARY OF THE INVENTION

The present disclosure is based, at least in part, on the development of antibodies having high binding affinity and specificity to the CD44 v7/8 splice variant. Such antibodies show inhibitory activity against cells expressing CD44 v7/8 (CD44+ cells).

Accordingly, one aspect of the present disclosure features an isolated antibody that binds to CD44 v7/8 (anti-CD44 v7/8 antibody), wherein the antibody specifically binds an epitope of human CD44 v7/8, wherein the epitope comprises the amino acid sequence of QAGRRMDMDSSHSIT (SEQ ID NO: 13). In some embodiments, an anti-CD44 v7/8 antibody binds the same epitope of human CD44 v7/8 as an exemplary antibody HIS029, the structural features of which are provided herein.

In some embodiments, an anti-CD44 v7/8 antibody does not bind peptide PISHPMGRGHQAGRR (SEQ ID NO: 12) or peptide SHSITLQPTANPNTG (SEQ ID NO: 14). In some embodiments, an anti-CD44 v7/8 antibody may comprise a heavy chain variable region ($V_H$), in which the heavy chain complementary determining region 1 (HC CDR 1), heavy chain complementary determining region 2 (HC CDR 2), and heavy chain complementary determining region 3 (HC CDR 3), collectively, are at least 85% (e.g., at least 90%, at least 95%, at least 98% or more) identical to the HC CDR1, HC CDR2, and HC CDR3 of antibody HIS029. In some instances, the antibody may comprise a $V_H$ that includes the same HC CDR1, HC CDR2, and HC CDR3 as antibody HIS029. In other embodiments, the anti-CD44 v7/8 antibody described herein may comprise a $V_H$ that comprises the HC CDR1, HC CDR2, and HC CDR3, which collectively contain up to 8 amino acid residue variations (7, 6, 5, 4, 3, 2, or 1 mutation(s)) relative to the HC CDR1, HC CDR2, and HC CDR3 of antibody HIS029.

Alternatively or in addition, the anti-CD44 v7/8 antibody described herein may comprise a light chain variable region ($V_L$), in which the a light chain complementary determining region 1 (LC CDR 1), a light chain complementary determining region 2 (LC CDR 2), and a light chain complementary determining region 3 (LC CDR 3), collectively, are at least 85% (e.g., at least 90%, at least 95%, at least 98% or more) identical to the LC CDR1, LC CDR2, and LC CDR3 of antibody HIS029. In some instances, the antibody may comprise the same LC CDR1, LC CDR2, and LC CDR3 as antibody HIS029. In other embodiments, the anti-CD44 v7/8 antibody described herein may comprise the LC CDR1, LC CDR2, and LC CDR3, which collectively contain up to 8 amino acid residue variations (7, 6, 5, 4, 3, 2, or 1 mutation(s)) relative to the LC CDR1, LC CDR2, and LC CDR3 of a reference antibody.

In some examples, the anti-CD44 v7/8 antibody described herein comprises the same heavy chain and/or light chain CDRs as antibody HIS029. In some instances, such an anti-CD44 v7/8 antibody may comprise the same $V_H$ and/or $V_L$ as antibody HIS029.

Any of the anti-CD44 v7/8 antibodies described herein may specifically binds to human CD44 v7/8. The antibody may be a human antibody or a humanized antibody. In some examples, it can be a chimeric antibody. In some embodiments, an anti-CD44 v7/8 antibody is a humanized antibody comprising a $V_H$ set forth as SEQ ID NO: 10, and/or a $V_L$ set forth as SEQ ID NO: 11.

In some embodiments, the anti-CD44 v7/8 antibody may be a full-length antibody (e.g., an IgG molecule) or an antigen-binding fragment thereof. Alternatively, it can be a single-chain antibody.

In another aspect, the present disclosure features a nucleic acid or set of nucleic acids (e.g., two nucleic acids), which collectively encodes any of the anti-CD44 v7/8 antibodies described herein, and a vector or set of vectors (e.g., two vectors) comprising the nucleic acid(s) coding for the anti-CD44 v7/8 antibodies. In some instances, the vector or vector set can be an expression vector(s). Also provided herein are host cells comprising the nucleic acid(s) or vector(s). Further, the present disclosure provides a method for making an anti-CD44 v7/8 antibody described herein, comprising culturing the host cell that comprises the vector or vector set comprising coding sequences for the antibody, wherein the coding sequences are in operably linkage to a suitable promoter, and harvesting the antibodies thus produced, for example, from the host cell or the culture medium.

In addition, the present disclosure provides an antibody-drug conjugate (ADC) comprising: any of the anti-CD44 v7/8 antibodies described herein, and at least one therapeutic agent, which is covalently conjugated to the antibody. In some examples, the therapeutic agent can be a cytotoxic agent, for example, monomethyl auristatin E.

In some embodiments, the antibody and the therapeutic agent may be conjugated through a linker. In some examples, the linker can be a cleavable linker, for example, a protease-sensitive linker, a pH-sensitive linker, or a glutathione-sensitive linker. In some instances, the linker can be a protease-sensitive linker, which may comprise a peptide having 2-5 amino acids. The peptide may comprise naturally-occurring amino acid residues, non-naturally-occurring amino acid residues, or a combination thereof. In one example, the peptide may comprise valine-citrulline. In other examples, the linker can be a non-cleavable linker. Such a non-cleavable linker may comprise an optionally substituted alkane or a thioether.

In some embodiments, the linker may comprise a functional group that forms a covalent bond between the antibody and the linker. Exemplary functional groups include, but are not limited to, a maleimide group, an iodoacetamide group, a vinyl sulfone group, an acrylate group, an acrylamide group, an acrylonitrile group, and a methacrylate group. In one example, the linker may further a molecular spacer of Formula I:

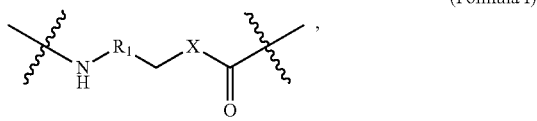
(Formula I)

in which
- R1 is optionally substituted C1-6 alkyl, optionally substituted phenyl, optionally substituted C2-6 alkylene, optionally substituted C2-6 alkenylene, optionally substituted C2-6 alkynylene, or optionally substituted triazole; and X is O, S, or N.

Further, the present disclosure provides a chimeric antigen receptor (CAR), which may comprise: (i) an extracellular domain comprising an antigen binding fragment that binds CD44 v7/8, (ii) a transmembrane domain, and (iii) one or more intracellular stimulatory domains. The antigen binding fragment may specifically binds an epitope of human CD44 v7/8, wherein the epitope comprises the amino acid sequence of QAGRRMDMDSSHSIT (SEQ ID NO: 13). In some embodiments, the antigen binding fragment does not bind peptide PISHPMGRGHQAGRR (SEQ ID NO: 12) or peptide SHSITLQPTANPNTG (SEQ ID NO: 14). In some examples, the antigen binding fragment may comprise the same HC CDRs and/or LC CDRs of any of the reference antibodies. Such an antigen binding fragment may comprise the same $V_H$ and $V_L$ of antibody HIS029. In some examples, the antigen binding fragment can be a single chain antibody (scFv).

In any of the CARs described herein, the transmembrane domain may comprise a transmembrane domain derived from CD28 or CD8. Alternatively or in addition, the one or more intracellular stimulatory domains may comprise a signaling domain from CD3ζ, a co-stimulatory domain, or a combination thereof. In some embodiments, a co-stimulatory signaling domain is from 4-1BB, CD7, CD27, CD28, CD40, OX40, ICOS, GITR, HVEM, TIM1, or LFA-1. Nucleic acids encoding any of the CAR described herein, vectors comprising such, and host cells expressing the CAR are also within the scope of the present disclosure. In some examples, the host cell expressing the CAR is an immune cell such as a T cell.

In yet another aspect, the present disclosure provides a pharmaceutical composition comprising (i) one or more of the anti-CD44 v7/8 antibodies described herein, a nucleic acid or set of nucleic acids encoding such, an antibody-drug conjugate comprising an anti-CD44 v7/8 antibody described herein, or a host cell expressing any of the nucleic acids or CAR constructs described herein, and (ii) a pharmaceutically acceptable carrier.

Moreover, the present disclosure features a method of inhibiting cells expressing CD44 v7/8, the method comprising administering to a subject in need thereof an effective amount of any of the pharmaceutical compositions described herein. In some embodiments, the subject may be a human patient has or is suspected of having cancer, for example, head and neck carcinoma, cervical cancer, and breast cancer.

Also within the scope of the present disclosure are pharmaceutical compositions as described herein for use in treating any of the target diseases also described herein (e.g., cancer such as head and neck carcinoma, cervical cancer, and breast cancer) or for use in manufacturing a medicament for the treatment of the target disease.

In addition, the present disclosure features a method of detecting presence of cells expressing CD44 v7/8, the method comprising: (i) contacting a sample suspected of having CD44$^+$ cells with any of the anti-CD44 v7/8 antibodies described herein, which is conjugated with a labeling agent; and (ii) detecting presence of cells expressing CD44 v7/8 in the sample based on binding of the antibody to cells in the sample. In some instances, the sample is derived from a human patient at risk for or suspected of having a cancer, such as head and neck carcinoma, cervical cancer, and breast cancer.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 1A: a table showing CD44 peptide sequences (CD44 v7; CD44 v7/8; and CD44 v8; SEQ ID NOs: 12, 13, and 14, respectively). FIG. 1B: a graph showing that CD44 v7/8 peptide is able to inhibit/block binding between HIS029 antibody and CD44$^+$ Detroit 562 (D562) cells, as evidenced by a loss of fluorescence upon addition of CD44 v7/8 peptide to a mixture of HIS029 antibody and Detroit 562 cells, which express CD44 v7/8 (CD44$^+$ cells).

FIG. 5A: graphs showing that anti-CD44 v7/8 CAR$^+$ T cells are effective at inducing secretion of interferon-gamma (IFN-g or IFNγ) when co-cultured with CD44$^+$ A523 cells. FIG. 5B: graphs showing that anti-CD44 v7/8 CAR$^+$ T cells are effective at inducing secretion of interleukin-2 (IL2) when co-cultured with CD44$^+$ A523 cells.

DETAILED DESCRIPTION OF THE INVENTION

Figure 1A:
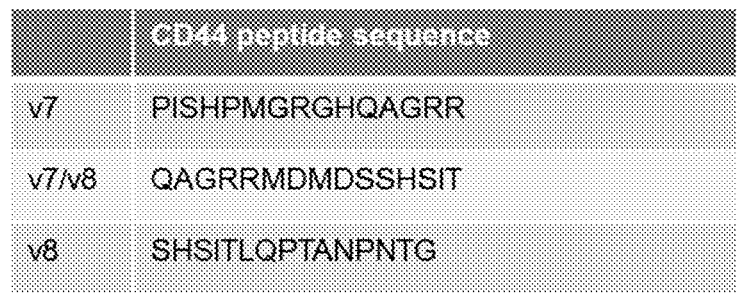
FIGS. 1A-1B includes diagrams showing binding specificity of antibody HIS029 to an epitope of the CD44 v7/8 splice variant.

CD44 variants are overexpressed in several cancers. For example, CD44 v7/8 is positively expressed in 64% of head and neck squamous cell carcinoma (HNSCC) patients, 11.5% of skin squamous cell carcinoma patients and 5% of cervical cancer patients. Accordingly, agents targeting the CD44 v7/8 variant (e.g., anti-CD44 v7/8 antibodies) are expected to be effective in both cancer treatment and diagnosis.

Disclosed herein are antibodies having binding specificity to the CD44 v7/8 splice variant and antibody-drug conjugates or chimeric antigen receptors comprising such. The anti-CD44 v7/8 antibody disclosed herein showed superior features, including high binding affinity and specificity to the CD44 v7/8 antigen, and/or high inhibitory activity against CD44+ cells.

Accordingly, provided herein are antibodies capable of binding to CD44 v7/8, nucleic acids encoding such, antibody-drug conjugates (ADCs) and chimeric antigen receptors (CARs) comprising the anti-CD44 v7/8 antibodies, and uses thereof for both therapeutic and diagnostic purposes. Also provided herein are kits for therapeutic and/or diagnostic use of the antibodies and/or ADCs and CARs comprising such, as well as methods for producing the anti-CD44 v7/8 antibodies.

Antibodies Binding to CD44 v7/8

The present disclosure provides antibodies that bind CD44, which is also known as HCAM (homing cell adhesion molecule), Pgp-1 (phagocytic glycoprotein-1), Hermes antigen, lymphocyte homing receptor, ECM-III, or HUTCH-1. CD44 is encoded by the CD44 gene (NCBI Gene ID: 960). In particular, the antibodies described herein have high binding specificity to CD44 v7/8, which is a splice variant comprising both exon 7 and exon 8.

CD44 is a cell-surface protein receptor that is involved in cellular adhesion, cell-cell interaction, lymphocyte activation, recirculation and homing, hematopoiesis, and tumor metastasis. CD44 exists in several variant forms resulting from alternative splicing. Of particular interest is the CD44 variant, CD44 v7/8, which comprises regions of CD44 transcribed from exons 7 and 8, and which is routinely expressed in several types of cancer, e.g., head and neck squamous cell carcinoma (HNSCC), skin squamous cell carcinoma, cervical cancer, and breast cancer patients. Thus this receptor can serve as a target and/or a biomarker for treatment and diagnosis of target cancer(s).

Accordingly, the anti-CD44 v7/8 antibodies disclosed herein may be used in treating and/or diagnosing a target cancer as described herein, either by itself or being conjugated to other moieties, for example, being conjugated to a therapeutic agent to form an antibody-drug conjugate or being the extracellular antigen-binding domain in a chimeric antigen receptor. Cell therapy targeting CD44+ cells is also within the present disclosure for eliminating disease cells that express cell surface CD44 v7/8.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. See, e.g., Kabat, E. A., et al. (1991) *Sequences of Proteins of Immunological Interest, Fifth Edition*, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs.

In some embodiments, the anti-CD44 v7/8 antibody as described herein can bind and inhibit the activity of CD44 v7/8, by at least 50% (e.g., 60%, 70%, 80%, 90%, 95% or greater). The apparent inhibition constant ($Ki^{app}$ or $K_{i,app}$), which provides a measure of inhibitor potency, is related to the concentration of inhibitor required to reduce enzyme activity and is not dependent on enzyme concentrations. The inhibitory activity of an anti-CD44 v7/8 antibody described herein can be determined by routine methods known in the art.

The $K_{i,}^{app}$ value of an antibody may be determined by measuring the inhibitory effect of different concentrations of the antibody on the extent of the reaction (e.g., enzyme activity); fitting the change in pseudo-first order rate constant (v) as a function of inhibitor concentration to the modified Morrison equation (Equation 1) yields an estimate of the apparent Ki value. For a competitive inhibitor, the $Ki^{app}$ can be obtained from the y-intercept extracted from a linear regression analysis of a plot of $K_{i,}^{app}$ versus substrate concentration.

$$v = A \cdot \frac{([E]-[I]-K_i^{app}) + \sqrt{([E]-[I]-K_i^{app})^2 + 4[E]\cdot K_i^{app}}}{2} \qquad \text{(Equation 1)}$$

Where A is equivalent to $v_o/E$, the initial velocity ($v_o$) of the enzymatic reaction in the absence of inhibitor (I) divided by the total enzyme concentration (E).

In some embodiments, the anti-CD44 v7/8 antibody described herein may have a Ki$^{app}$ value of 1000, 900, 800, 700, 600, 500, 400, 300, 200, 100, 50, 40, 30, 20, 19, 18, 17, 16, 15, 14, 13, 12, 11, 10, 9, 8, 7, 6, 5 pM or less for a CD44 epitope, a CD44 v7/8 antigen or an antigenic epitope thereof. In some embodiments, the anti-CD44 v7/8 antibody may have a lower Ki$^{app}$ for a first target relative to a second target. Differences in Ki$^{app}$ (e.g., for specificity or other comparisons) can be at least 1.5, 2, 3, 4, 5, 10, 15, 20, 37.5, 50, 70, 80, 91, 100, 500, 1000, 10,000 or 10$^5$ fold.

The antibodies described herein can be murine, rat, human, or any other origin (including chimeric or humanized antibodies). Such antibodies are non-naturally occurring, i.e., would not be produced in an animal without human act (e.g., immunizing such an animal with a desired antigen or fragment thereof).

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In one example, the antibody used in the methods described herein is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, and/or six), which are altered with respect to the original antibody, which are also termed one or more CDRs "derived from" one or more CDRs from the original antibody. Humanized antibodies may also involve affinity maturation.

In another example, the antibody described herein can be a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the anti-CD44 v7/8 antibodies described herein specifically bind to the corresponding target antigen or an epitope thereof. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to a CD44 v7/8 antigen or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen. In some embodiments, the anti-CD44 v7/8 antibody described herein specifically binds human CD44. In some embodiments, the anti-CD44 v7/8 antibody described herein specifically binds human CD44 v7/8. In some examples, its binding activity to a non-human CD44 v7/8, antigen is not detectable in a conventional assay or is very low such that it would have no significant biological significance as known to those skilled in the art. In other examples, the anti-CD44 v7/8 antibody described herein may cross-react with CD44 v7/8 from different species, for example, between human CD44 v7/8 and a non-human CD44 v7/8 (e.g., CD44 v7/8 from an experimental animal such as a non-human primate, mouse, or rat).

As used herein, the term "CD44", "CD44 v7/8", or "HCAM" refers to a CD44 of any suitable species, e.g., human, a non-human mammal such as a non-human primate, or a rodent (e.g., mouse or rat). CD44 v7/8 is a splice variant of a cell-surface glycoprotein that functions primarily in cell adhesion, cell-cell interactions, and as a protein receptor for ligands such as hyaluronic acid. The amino acid sequence of an exemplary human CD44 v7/8 splice variant is provided below, with a v7/8 epitope targeted by exemplary antibodies described herein labeled in bold (see also NCBI accession no. NP_000601.3):

(SEQ ID NO: 1)

```
  1    mdkfwwhaaw glclvplsla qidlnitcrf agvfhvekng rysisrteaa dlckafnstl 61    ptmaqmekal sigfetcryg fieghvvipr ihpnsicaan ntgvyiltsn tsqydtycfn 121    asappeedct svtdlpnafd gpititivnr dgtryvqkge yrtnpediyp snptdddvss
```

-continued

```
181    gssserssts  ggyifytfst  vhpipdedsp  witdstdrip  attlmstsat  atetatkrqe 241    twdwfswlfl  psesknhlht  ttqmagtssn  tisagwepne  enederdrhl  sfsgsgiddd 301    edfisstist  tprafdhtkq  nqdwtqwnps  hsnpevllqt  ttrmtdvdrn  gttayegnwn 361    peahpplihh  ehheeeetph  ststiqatps  stteetatqk  eqwfgnrwhe  gyrqtpkeds 421    hsttgtaaas  ahtshpmqgr  ttpspedssw  tdffnpishp  mgrghqagrr  mdmdsshsit

481    lqptanpntg  lvedldrtgp  lsmttqqsns  qsfstshegl  eedkdhptts  tltssnrndv 541    tggrrdpnhs  egsttllegy  tshyphtkes  rtfipvtsak  tgsfgvtavt  vgdsnsnvnr 601    slsgdqdtfh  psggshtthg  sesdghshgs  qegganttsg  pirtpqipew  liilasllal 661    alilavciav  nsrrrcgqkk  klvinsgnga  vedrkpsgln  geasksqemv  hlvnkesset 721    pdqfmtadet  rnlqnvdmki  gv
```

CD44 v7/8 molecules from other species were well known in the art and the amino acid sequences thereof can be retrieved from a publically available database, for example, GenBank or NCBI.

In some embodiments, an anti-CD44 v7/8 antibody as described herein has a suitable binding affinity for the target antigen (e.g., human CD44 v7/8) or antigenic epitopes thereof. As used herein, "binding affinity" refers to the apparent association constant or KA. The KA is the reciprocal of the dissociation constant ($K_D$). The anti-CD44 v7/8 antibody described herein may have a binding affinity ($K_D$) of at least $10^{-5}$, $10^{-6}$, $10^{-7}$, $10^{-8}$, $10^{-9}$, $10^{-10}$ M, or lower for the target antigen or antigenic epitope. An increased binding affinity corresponds to a decreased $K_D$. Higher affinity binding of an antibody for a first antigen relative to a second antigen can be indicated by a higher KA (or a smaller numerical value $K_D$) for binding the first antigen than the KA (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). In some embodiments, the anti-CD44 v7/8 antibodies described herein have a higher binding affinity (a higher KA or smaller $K_D$) to human CD44 v7/8, as compared to the binding affinity to CD44 v7/8 of a different species. Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold. In some embodiments, any of the anti-CD44 v7/8 antibodies may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

$$[Bound]=[Free]/(Kd+[Free])$$

It is not always necessary to make an exact determination of KA, though, since sometimes it is sufficient to obtain a quantitative measurement of affinity, e.g., determined using a method such as ELISA or FACS analysis, is proportional to KA, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the anti-CD44 v7/8 antibodies described herein bind to the same epitope in a CD44 v7/8, antigen (e.g., human CD44 v7/8) as one of the reference antibodies provided herein or compete against the reference antibody from binding to the CD44 v7/8 antigen. Reference antibodies provided herein include HIS029, the structural features of which are provided herein. An antibody that binds the same epitope as a reference antibody described herein may bind to exactly the same epitope or a substantially overlapping epitope (e.g., containing less than 3 non-overlapping amino acid residue, less than 2 non-overlapping amino acid residues, or only 1 non-overlapping amino acid residue) as the reference antibody. Whether two antibodies compete against each other from binding to the cognate antigen can be determined by a competition assay, which is well known in the art. Such antibodies can be identified as known to those skilled in the art, e.g., those having substantially similar structural features (e.g., complementary determining regions), and/or those identified by assays known in the art. For example, competition assays can be performed using one of the reference antibodies to determine whether a candidate antibody binds to the same epitope as the reference antibody or competes against its binding to the CD44 v7/8 antigen. In some embodiments, the anti-CD44 v7/8 antibodies described herein specifically bind an epitope of human CD44 v7/8, wherein the epitope comprises the amino acid sequence of QAGRRMDMDSSHSIT (SEQ ID NO: 13).

In some instances, the anti-CD44 v7/8 antibodies described herein do not bind to a peptide PISHPMGRGHQAGRR (SEQ ID NO: 12) or peptide SHSITLQPTANPNTG (SEQ ID NO: 14). An antibody that does not bind an antigen means that no meaningful binding (e.g., only background binding or no binding at all) can be detected using a conventional assay (e.g., ELISA or surface plasmon resonance).

The anti-CD44 v7/8 antibodies described herein may comprise a heavy chain variable region ($V_H$), which may comprise (a) a heavy chain complementary determining region 1 (HC CDR 1) as in HIS029 OR humanized HIS029; (b) a heavy chain complementary determining region 2 (HC CDR2) as in HIS029 OR humanized HIS029; (c) a heavy chain complementary determining region 3 (HC CDR3) as in HIS029 OR humanized HIS029; or (d) a combination of any one of (a)-(c). In some instances, the antibody may comprise a HC CDR1 of (a), a HC CDR2 of (b), and a HC CDR3 of (c).

Table 1 provides the amino acid sequences of the heavy chain CDRs (by IMGT definitions) for exemplary anti-CD44 v7/8 antibodies. Antibodies having the same heavy chain CDR1, CDR2, and CDR3 regions as those exemplary anti-CD44 v7/8 antibodies are within the scope of the present disclosure.

```
HIS029
V_H (SEQ ID NO: 8):
QVHLQQPGAELVRPGASVKLSCKASGYTFTNYWINWVKQRPGQGLEWIG
NIYPSDSYTNYNQKFKDKATLTVDKSSSTAYVHLSSPTSEDSAVYYC**TK
WGDSDY**WGQGTTLTVSS

V_L (SEQ ID NO: 9):
DIKMTQSFSSMYASLGERVTITCKASQDINRYLRWFQQKFGKSPKTLIY
RANRLVDGVFSRFSGSGSGQDYSLTISSLEYEDMGIYYCLQYDEFPFTF
GSGTKLEIK
```

Also within the scope of the present disclosure are functional variants of any of the reference anti-CD44 v7/8 antibodies as disclosed herein (e.g., those listed in Tables 1 and 2 above). A functional variant can comprise up to 8 (e.g., 7, 6, 5, 4, 3, 2, or 1) amino acid residue variations in one or more of the heavy chain and light chain CDR regions of the reference antibody and binds the same epitope of the CD44

TABLE 1

Heavy chain CDR sequences of reference anti-CD44 v7/8 antibodies

| Exemplary Antibody | CDR1 | CDR2 | CDR3 |
| --- | --- | --- | --- |
| HIS029 | GYTFTNYW (SEQ ID NO: 2) | IYPSDSYT (SEQ ID NO: 3) | TKWGDSDY (SEQ ID NO: 4) |

Alternatively or in addition, the anti-CD44 v7/8 antibodies described herein may comprise a light chain variable domain ($V_L$) that comprises a light chain variable region ($V_L$), which comprises (a) a light chain complementary determining region 1 (LC CDR 1) as in HIS029 OR humanized HIS029; (b) a light chain complementary determining region 2 (LC CDR2) as in HIS029 OR humanized HIS029; (c) a light chain complementary determining region 3 (LC CDR3) as in HIS029 OR humanized HIS029; or (d) any combination of (a)-(c).

Table 2 provides the amino acid sequences of the light chain CDRs for exemplary anti-CD44 v7/8 antibodies. Antibodies having the same light chain CDR1, CDR2, and CDR3 regions as those exemplary anti-CD44 v7/8 antibodies are within the scope of the present disclosure.

v7/8 antigen with substantially similar affinity (e.g., having a $K_D$ value in the same order). In some instances, each of the heavy chain and/or light chain CDR in a functional variant contain no more than 2 amino acid residue variations as relative to the counterpart CDR in the reference antibody. In some examples, each of the heavy chain and/or light chain CDR in a functional variant contain no more than 1 amino acid residue variations as relative to the counterpart CDR in the reference antibody.

In one example, the amino acid residue variations are conservative amino acid residue substitutions. As used herein, a "conservative amino acid substitution" refers to an amino acid substitution that does not alter the relative charge or size characteristics of the protein in which the amino acid substitution is made. Variants can be prepared according to

TABLE 2

Light chain CDR sequences of reference anti-CD44 v7/8 antibodies

| Exemplary Antibody | CDR1 | CDR2 | CDR3 |
| --- | --- | --- | --- |
| HIS029 | QDINRY (SEQ ID NO: 5) | RAN (SEQ ID NO: 6) | LQYDEFPFT (SEQ ID NO: 7) |

The heavy chain and light chain CDRs of the reference antibodies provided herein are determined based on the IMGT approach, which is well known in the art. In some instances, the anti-CD44 v7/8 antibodies disclosed herein may comprise the same heavy chain and light chain CDRs of any of the reference antibodies disclosed herein. Two antibodies having the same $V_H$ and/or $V_L$ CDRs means that their CDRs are identical when determined by the same approach (e.g., those described herein and/or known in the art).

In some examples, the anti-CD44 v7/8 antibodies disclosed herein may comprise the same $V_H$ and/or $V_L$ sequence as the reference antibodies, which are provided below (CDRs in boldface):

methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the anti-CD44 v7/8 antibody comprises heavy chain CDRs that, individually or collectively, are at least 80% (e.g., 85%, 90%, 95%, or 98%) identical to the heavy chain CDRs of a reference antibody (e.g., HIS029), and/or light chain CDRs that, individually or collectively, are at least 80% (e.g., 85%, 90%, 95%, or 98%) identical to the light chain CDRs of the reference antibody. In some embodiments, the anti-CD44 v7/8 antibody comprises a heavy chain variable region ($V_H$) that is at least 80% (e.g., 85%, 90%, 95%, or 98%) identical to the heavy chain variable region of any of the reference antibody and/or a light chain variable region ($V_L$) that is at least 80% (e.g., 85%, 90%, 95%, or 98%) identical to the light chain variable region of the reference antibody.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

"Individually" means that one particular heavy chain or light chain CDR of an antibody shares the described sequence identify to the corresponding heavy chain or light chain CDR of an exemplary antibody, e.g., HIS029. "Collectively" means that the three heavy chain or light chain CDRs of an antibody, in combination, share the described sequence identity to the three corresponding heavy chain or light chain CDRs of an exemplary antibody, e.g., HIS029.

The present disclosure also provides germlined variants of any of the reference anti-CD44 v7/8 antibodies disclosed herein. A germlined variant contains one or more mutations in the framework regions as relative to its parent antibody towards the corresponding germline sequence. To make a germline variant, the heavy or light chain variable region sequence of the parent antibody or a portion thereof (e.g., a framework sequence) can be used as a query against an antibody germline sequence database (e.g., bioinfo.org.uk/abs/, vbase2.org, or imgt.org) to identify the corresponding germline sequence used by the parent antibody and amino acid residue variations in one or more of the framework regions between the germline sequence and the parent antibody. One or more amino acid substitutions can then be introduced into the parent antibody based on the germline sequence to produce a germlined variant.

In some instances, the functional variant of a reference antibody disclosed herein is a humanized antibody of the reference antibody. Examples include:

```
Humanized HIS029
V_H (SEQ ID NO: 10):
QVQLVQSGSELKKPGASVKVSCKASGYTFTNYWINWVRQAPGQGLEWMG
NIYPSDSYTNYNQKFKDRAVFSVDKSVSTAYLQISSLKAEDTAVYYC**TK
WGDSDY**WGQGTTVTVSS V_L (SEQ ID NO: 11):
DIQMTQSPSSLSASVGDRVTITCKASQDINRYLRWFQQKPGKSPKTLIY
RANRLVDGVPSRFSGSGSGQDYTLTISSLQPEDFATYYCLQYDEFPFTF
GQGTKLEIK
```

In some embodiments, the heavy chain of any of the anti-CD44 v7/8 antibodies as described herein may further comprise a heavy chain constant region (HC) or a portion thereof (e.g., HC1, HC2, HC3, or a combination thereof).

The heavy chain constant region can of any suitable origin, e.g., human, mouse, rat, or rabbit. In one specific example, the heavy chain constant region is from a human IgG (a gamma heavy chain). When needed, the anti-CD44 v7/8 antibody as described herein may comprise a modified constant region. For example, it may comprise a modified constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the anti-CD44 v7/8 antibodies described herein may further comprise a light chain that includes a light chain variable region and optionally, a light chain constant region, which can be any LC known in the art. In some examples, the LC is a kappa light chain. In other examples, the LC is a lambda light chain. Antibody heavy and light chain constant regions are well known in the art, e.g., those provided in the IMGT database (imgt.org) or at vbase2.org/vb-stat.php., both of which are incorporated by reference herein.

Preparation of Anti-CD44 v7/8 Antibodies

Antibodies capable of binding CD44 v7/8 as described herein can be made by any method known in the art. See, for example, Harlow and Lane, (1998) Antibodies: A Laboratory Manual, Cold Spring Harbor Laboratory, New York.

In some embodiments, antibodies specific to a target CD44 v7/8 antigen (e.g., human CD44) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-CD44 v7/8 monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the CD44 v7/8 activity. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of CD44. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

In some embodiments, antibodies capable of binding to a CD44 v7/8, antigen can be isolated from an antibody library, for example, a phage display antibody library or a yeast display antibody library. In one example, the anti-CD44 v7/8 antibody described herein can be isolated from a monoclonal antibody library, for example, following the methods disclosed in US 2015/0153356, the relevant disclosures of which are incorporated by reference herein for the purposes or subject matter referenced herein.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., Proc. Natl. Acad. Sci. USA, 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library and scFv clones specific to a CD44 v7/8, can be identified from the library following routine procedures. Positive clones can be subjected to further screening to identify those that inhibit CD44 v7/8, activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the CD44 v7/8, polypeptide have been replaced (swapped) with sequences from a closely related, but antigenically distinct protein. By assessing binding of the antibody to the mutant CD44, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

In some examples, an anti-CD44 v7/8 antibody is prepared by recombinant technology as exemplified below.

Nucleic acids encoding the heavy and light chain of an anti-CD44 v7/8 antibody as described herein can be cloned into one expression vector, each nucleotide sequence being in operable linkage to a suitable promoter. In one example, each of the nucleotide sequences encoding the heavy chain and light chain is in operable linkage to a distinct prompter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, E. coli lac UV5 promoter, and the herpes simplex tk virus promoter.

Regulatable promoters can also be used. Such regulatable promoters include those using the lac repressor from E. coli as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from E. coli can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells transactivator or repressor fusion protein, which in some instances can be toxic to cells (Gossen et al., Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-CD44 v7/8 antibody, as also described herein. The recombinant expression vector can be introduced into a suitable host cell (e.g., a dhfr-CHO cell) by a conventional method, e.g., calcium phosphate-mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-CD44 v7/8 antibody and the other encoding the light chain of the anti-CD44 v7/8 antibody. Both of the two recombinant expression vectors can be introduced into a suitable host cell (e.g., dhfr-CHO cell) by a conventional method, e.g., calcium phosphate-mediated transfection. Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-CD44 v7/8 antibody as described herein, vectors (e.g., expression vectors) containing such; and host cells comprising the vectors are within the scope of the present disclosure.

Antibody-Drug Conjugate

The present disclosure also provides antibody-drug conjugates comprising any of the anti-CD44 v7/8 antibodies described herein, which is in covalent linkage to a therapeutic agent.

The term "antibody-drug conjugate" or "ADC" used herein refers to a conjugate wherein the anti-CD44 v7/8 antibody described herein and a therapeutic agent are covalently linked. Generally, this antibody-drug conjugate may include the anti-CD44 v7/8 antibody, the therapeutic agent, and optionally a linker between the antibody and the therapeutic agent. The ADC may increase therapeutic effects by delivering the therapeutic agent to a $CD44^+$ cell, which is targeted by the antibody, in particular, a $CD44^+$ cancer cell. The antibody-drug conjugate may be prepared by various methods of preparing antibody-drug conjugates, which are known in the art.

The therapeutic agent in the ADC described herein may be a toxin, a chemotherapeutic agent, an antibiotic, ADP-ribosyl transferase, a radioactive isotope or a nucleolytic enzyme. In some instances, the therapeutic agent is a cytotoxic agent. Examples include, but are not limited to, anthracycline, an auristatin (e.g., auristatin E or monomethyl auristatin E (MMAE)), a camptothecin, a combretastain, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, a pladienolide, and calicheamicin.

In some embodiments, the anti-CD44 v7/8 antibody and the therapeutic agent are connected via a linker. Such a linker may be a cleavable linker, for example, cleavable under a certain pH condition (a pH-sensitive linker), cleavable by a protease (a protease-sensitive linker), or cleavable in the presence of glutathione (a glutathione-sensitive linker). In some examples, the linker comprises a protease cleavage site, which may contain 2-5 amino acid residues that are recognizable and/or cleavable by a suitable protease. Such a peptide may comprise naturally-occurring amino acid residues, non-naturally occurring amino acid residues, or a combination thereof. In one example, the peptide linker can be a dipeptide linker. Examples include a valine-citrulline (val-cit) linker, a phenylalanine-lysine (phe-lys) linker, or maleimidocapronic-valine-citruline-p-aminobenzyloxycarbonyl (vc) linker. Alternatively, the linker may be non-cleavable, e.g., a linker comprising optionally substituted alkane or thioether.

In some examples, the linker may comprise a functional group that can form a covalent bond with the antibody. Exemplary functional groups include, but are not limited to, a maleimide group, an iodoacetamide group, a vinyl sulfone group, an acrylate group, an acrylamide group, an acrylonitrile group, or a methacrylate group. In some instances, the linker can contain one or more reactive amines include, but are not limited to, acetyl-lysine-valine-citrulline-p-aminobenzyloxycarbonyl (AcLys-VC-PABC) or amino PEG6-propionyl. See, e.g., WO2012/059882. Other exemplary linkers include Sulfosuccinimidyl-4-[Nmaleimidomethyl] cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N terminus).

In some examples, the linker may comprise a molecular spacer, for example, a moiety of Formula I:

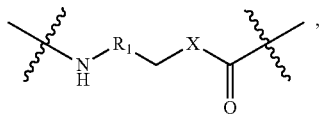

in which $R_1$ can be optionally substituted $C_{1-6}$ alkyl (e.g., $C_{1-3}$ alkyl), optionally substituted phenyl, optionally substituted $C_{2-6}$ alkylene, optionally substituted $C_{2-6}$ alkenylene, optionally substituted $C_{2-6}$ alkynylene, or optionally substituted triazole; and/or X can be O, S, or N.

Methods for conjugating cytotoxic agent or other therapeutic agents to antibodies were known in the art and have been described in various publications. For example, chemical modification can be made in the antibodies either through lysine side chain amines or through cysteine sulfhydryl groups activated by reducing interchain disulfide bonds for the conjugation reaction to occur. See, e.g., Tanaka et al., FEBS Letters 579:2092-2096, (2005), and Gentle et al., Bioconjug. Chem. 15:658-663, (2004). Reactive cysteine residues engineered at specific sites of antibodies for specific drug conjugation with defined stoichiometry have also been described. See, e.g., Junutula et al., Nature Biotechnology, 26:925-932, (2008). Conjugation using an acyl donor glutamine-containing tag and/or an endogenous glutamine made reactive by polypeptide engineering in the presence of transglutaminase and an amine, for example, a cytotoxic agent modified with a reactive amine, is also described in WO2012/059882, Strop et al., Chem. Biol. 20(2):161-167 (2013), and Farias et al., Bioconjug. Chem. 25(2):245-250 (2014). The relevant disclosures of such publications are herein incorporated by reference for the purpose and subject matter referenced therein.

Chimeric Antigen Receptor (CAR) and Immune Cells Expressing Such

The present disclosure also features chimeric antigen receptors targeting CD44 v7/8 and immune cells expressing such. Chimeric antigen receptors (CARs) as disclosed herein are artificial cell-surface receptors that redirect binding specificity of immune cells (e.g., T cells) expressing such to $CD44^+$ cells, such as cancer cells derived from head and neck carcinoma, cervical cancer, and breast cancer, thereby eliminating the target disease cells via, e.g., the effector activity of the immune cells. A CAR construct often comprises an extracellular antigen binding domain fused to at least an intracellular signaling domain. Cartellieri et al., J Biomed Biotechnol 2010:956304, 2010. The extracellular antigen binding domain, which can be a single-chain antibody fragment (scFv), is specific to a CD44 v7/8, antigen and the intracellular signaling domain can mediate a cell signaling that lead to activation of immune cells. As such, immune cells expressing a CAR construct specific to CD44 v7/8 can bind to diseased cells (e.g., tumor cells) expressing CD44, leading to activation of the immune cells and elimination of the diseased cells.

Any of the anti-CD44 v7/8 antibodies described herein can be used to produce the CAR constructs also described herein. For example, the $V_H$ and $V_L$ domains of an anti-CD44 v7/8 antibody can be fused to the intracellular signaling domain(s) to produce a CAR construct using the conventional recombinant technology. In some examples, the $V_H$ and $V_L$ domains of an anti-CD44 v7/8 are connected via a peptide linker to form a scFv fragment.

The CAR construct disclosed herein may comprise one or more intracellular signaling domains. In some examples, CAR comprises an intracellular signaling domain that includes an immunoreceptor tyrosine-based activation motif (ITAM). Such an intracellular signaling domain may be from CD3ζ. In addition, the CAR construct may further comprise one or more co-stimulatory signaling domains, which may be from a co-stimulatory receptor, for example, from 4-1BB (CD137), CD7, CD27, CD28, CD40, OX40, ICOS, GITR, HVEM, TIM1, or LFA-1.

The CAR construct disclosed herein may further comprise a transmembrane-hinge domain, which can be obtained from a suitable cell-surface receptor, for example, CD28 or CD8.

Also provided are isolated nucleic acid molecules and vectors encoding any of the anti-CD44 v7/8 CARs as disclosed herein, and host cells, such as host immune cells (e.g., T cells and natural killer cells), comprising the nucleic acid molecules or vectors. Immune cells expressing anti-CD44 v7/8 CARs, which comprises a CD44-specific antibody binding fragment, can be used for the treatment of cancers that express CD44. Thus, also provided herein are methods of treating a subject with $CD44^+$ cancer by selecting a subject with a cancer that expresses CD44, and administering to the subject a therapeutically effective amount of the immune cells expressing the CD44-targeted CARs.

Pharmaceutical Compositions

The anti-CD44 v7/8 antibodies, the encoding nucleic acids or nucleic acid sets, vectors comprising such, or host cells comprising the vectors, as described herein, as well as the ADCs comprising the anti-CD44 v7/8 antibodies and/or immune cells expressing CD44-targeting CARs, can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some examples, the pharmaceutical composition described herein comprises liposomes containing the antibodies (or the encoding nucleic acids, or the ADCs), which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, the encoding nucleic acid(s), or the ADCs may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulised solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

Methods of Treatment and Diagnosis

Any of the anti-CD44 v7/8 antibodies, the encoding nucleic acids or nucleic acid sets, vectors comprising such, the ADCs comprising the anti-CD44 v7/8 antibodies, and immune cells (e.g., T cells or NK cells) expressing CD44-targeting CARs, as described herein, are useful for inhibiting and/or eliminating $CD44^+$ disease cells, such as $CD44^+$ cancer cells, thereby benefiting treatment of a disease or disorder associated with the $CD44^+$ disease cells.

To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder associated with $CD44^+$ disease cells. In some embodiments, the $CD44^+$ disease cells are cancer cells, for example, head and neck carcinoma cells, cervical cancer cells, and breast cancer cells. A subject having a target disease or disorder can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors for that disease/disorder.

As used herein, "an effective amount" refers to the amount of each active agent required to confer therapeutic effect on the subject, either alone or in combination with one or more other active agents. In some embodiments, the therapeutic effect is reduced CD44 v7/8, activity or the activity of $CD44^+$ cells. Determination of whether an amount of the antibody or other therapeutic agents comprising such (e.g., ADC or CAR-T cells) achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of any of the anti-CD44 v7/8 antibodies or ADCs comprising such as described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

For the purpose of the present disclosure, the appropriate dosage of an antibody as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the antagonist, and the discretion of the attending physician. Typically the clinician will administer an antibody, until a dosage is reached that achieves the desired result. In some embodiments, the desired result is a decrease in thrombosis. Methods of determining whether a dosage resulted in the desired result would be evident to one of skill in the art. Administration of one or more antibodies can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the antibodies described herein are administered to a subject in need of the treatment at an amount sufficient to inhibit the activity of one or both of the target antigen by at least 20% (e.g., 30%, 40%, 50%, 60%, 70%, 80%, 90% or greater) in vivo. In other embodiments, the antibodies are administered in an amount effective in reducing the activity level of a target antigens by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethylformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., those encoding the antibodies described herein) are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, i.e., dose, timing and repetition, used in the method described herein will depend on the particular subject and that subject's medical history.

When immune cells expressing a CD44-targeting CAR are used for disease treatment, patients can be treated by infusing therapeutically effective doses of such immune cells such as T lymphocytes or NK cells in the range of about $10^5$ to $10^{10}$ or more cells per kilogram of body weight (cells/Kg). The infusion can be repeated as often and as many times as the patient can tolerate until the desired response is achieved. The appropriate infusion dose and schedule will vary from patient to patient, but can be determined by the treating physician for a particular patient. Typically, initial doses of approximately $10^6$ cells/Kg will be infused, escalating to $10^8$ or more cells/Kg. IL-2 can be co-administered to expand infused cells. The amount of IL-2 can about $1-5 \times 10^6$ international units per square meter of body surface.

In some embodiments, more than one antibody, or a combination of an antibody and another suitable therapeutic agent, may be administered to a subject in need of the treatment. The antibody, ADCs and/or CAR-T cells comprising such, can also be used in conjunction with other agents that serve to enhance and/or complement the effectiveness of the agents.

Treatment efficacy for a target disease/disorder can be assessed by methods well-known in the art.

Any of the anti-CD44 v7/8 antibodies described herein may also be used for detecting the presence or level of CD44$^+$ cells in a sample. Such a diagnostic assay may be performed in vitro or in vivo.

For diagnostic uses, an anti-CD44 v7/8 antibody as described herein may be conjugated with a detectable label (e.g., an imaging agent such as a contrast agent) for diagnostic purposes, either in vivo or in vitro. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker. Conjugated or attached can include covalent or noncovalent bonding as well as other forms of association, such as entrapment, e.g., of one entity on or within the other, or of either or both entities on or within a third entity, such as a micelle.

In one example, an anti-CD44 v7/8 antibody as described herein can be attached to a detectable label, which is a compound that is capable of releasing a detectable signal, either directly or indirectly, such that the aptamer can be detected, measured, and/or qualified, in vitro or in vivo. Examples of such "detectable labels" are intended to include, but are not limited to, fluorescent labels, chemiluminescent labels, colorimetric labels, enzymatic markers, radioactive isotopes, and affinity tags such as biotin. Such labels can be conjugated to the aptamer, directly or indirectly, by conventional methods.

In some embodiments, the detectable label is an agent suitable for imaging CD44$^+$ cells in vivo, which can be a radioactive molecule, a radiopharmaceutical, or an iron oxide particle. Radioactive molecules suitable for in vivo imaging include, but are not limited to, $^{122}$I, $^{123}$I, $^{124}$I, $^{125}$I, $^{131}$I, $^{18}$F, $^{75}$Br, $^{76}$Br, $^{76}$Br, $^{77}$Br, $^{211}$At, $^{225}$Ac, $^{177}$Lu, $^{153}$Sm, $^{186}$Re, $^{188}$Re, $^{67}$Cu, $^{213}$Bi, $^{212}$Bi, $^{212}$Pb, and $^{67}$Ga. Exemplary radiopharmaceuticals suitable for in vivo imaging include $^{111}$In Oxyquinoline, $^{131}$I Sodium iodide, $^{99m}$Tc Mebrofenin, and $^{99m}$Tc Red Blood Cells, $^{123}$I Sodium iodide, $^{99m}$Tc Exametazime, $^{99m}$Tc Macroaggregate Albumin, $^{99m}$Tc Medronate, $^{99m}$Tc Mertiatide, $^{99m}$Tc Oxidronate, $^{99m}$Tc Pentetate, $^{99m}$Tc Pertechnetate, $^{99m}$Tc Sestamibi, $^{99m}$Tc Sulfur Colloid, $^{99m}$Tc Tetrofosmin, Thallium-201, and Xenon-133. The reporting agent can also be a dye, e.g., a fluorophore, which is useful in detecting a disease mediated by CD44$^+$ cells in tissue samples.

To perform a diagnostic assay in vitro, an anti-CD44 v7/8 antibody can be brought in contact with a sample suspected of containing CD44$^+$ cells. The antibody and the sample may be incubated under suitable conditions for a suitable period to allow for binding of the antibody to the CD44 v7/8, antigen. Such an interaction can then be detected via routine methods, e.g., ELISA or FACS. To perform a diagnostic assay in vivo, a suitable amount of anti-CD44 v7/8 antibodies, conjugated with a label, can be administered to a subject in need of the examination. Presence of the labeled antibody can be detected based on the signal released from the label by routine methods.

Kits for Use in Treatment and Diagnosis

The present disclosure also provides kits for use in inhibiting and/or eliminating CD44$^+$ disease cells and thus alleviating diseases/disorders associated with such disease cells. Such kits can include one or more containers comprising an anti-CD44 v7/8 antibody, an ADC comprising such, or immune cells expressing CD44-targeting CAR polypeptide, e.g., any of those described herein.

In some embodiments, the kit can comprise instructions for use in accordance with any of the methods described herein. The included instructions can comprise a description of administration of the anti-CD44 v7/8 antibody, the ADC, or the immune cells to treat, delay the onset, or alleviate a target disease as those described herein. The kit may further comprise a description of selecting an individual suitable for treatment based on identifying whether that individual has the target disease. In still other embodiments, the instructions comprise a description of administering an antibody, an ADC, or immune cells, to an individual at risk of the target disease.

The instructions relating to the use of an anti-CD44 v7/8 antibody, an ADC comprising such, or immune cells expressing CD44-targeting CAR, generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with CD44$^+$ cells, such as head and neck carcinoma, cervical cancer, and breast cancer. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-CD44 v7/8 antibody, an ADC comprising such, or immune cells expressing CD44-targeting CAR as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

Also provided herein are kits for use in detecting CD44$^+$ cells in a sample. Such a kit may comprise any of the anti-CD44 v7/8 antibodies described herein. In some instances, the anti-CD44 v7/8 antibody can be conjugated with a detectable label as those described herein. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker. Conjugated or attached can include covalent or noncovalent bonding as well as other forms of association, such as entrapment, e.g., of one entity on or within the other, or of either or both entities on or within a third entity, such as a micelle.

Alternatively or in addition, the kit may comprise a secondary antibody capable of binding to anti-CD44 v7/8 antibody. The kit may further comprise instructions for using the anti-CD44 v7/8 antibody for detecting CD44$^+$, particularly CD44 v7/8.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); Nucleic Acid Hybridization (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Generation of Anti-CD44 v7/8 Antibodies

Reagents and General Methods

Hybridoma cell culture medium (PFHM-II Protein-Free Hybridoma Medium; Ser. No. 12/040,077) was purchased from Thermo Fisher.

RNAs were isolated using standard protocols and the TRIzol Reagent from Thermo Fisher (#15596018). Resultant cDNA molecules were generated using the cDNA synthesis kit (PrimeScript II 1st strand cDNA synthesis kit; #6210A) from Takara. Antibody V-region amplification was performed using Premix Taq (#RR901A) from Takara. Standard PCR primer sets (Ig-Primer Sets #TB326) were obtained from Novagen. Genes were cloned into pET28a (Novagen; #69864) using standard techniques, including use of EcoRI, HindIII, SalI, and T4 Ligase (all from NEB). QIAEX II Gel Extraction Kit (QIAgen #20021) was utilized to purify some, but not all, oligonucleotide molecules.

A253, A375, A549, and Detroit 562 (D562) cell cultures were maintained in vitro as independent monolayer cultures at 37° C. in an atmosphere of 5% $CO_2$. These tumor cells were passaged regularly, as needed.

Screening of an Antibody Library to Identify Anti-CD44 v7/8 Antibodies

As previously described in US 2015/0153356, a large library of monoclonal antibodies (>100,000 in total) was generated using a mixture of proteome and peptide antigens. The library was segmented into a series of high density antibody arrays before being screened against cancer tumor samples and the FDA Normal Tissue Panel.

A number of antibodies isolated from the library, including HIS029, were found to differentially target the D562 cell line ($CD44^+$-expressing). CD44 v7/8 was identified as the target antigen via immunoprecipitation with the antibodies followed by mass spectroscopy.

Production of Antibody Clones

Individual hybridoma clones were cultured in a T25 flask with 10 mL hybridoma cell culture medium (PFHM-II Protein-Free Hybridoma Medium). Cells were grown at 37° C. until 80% confluent. Culture medium was then removed and cells were twice washed with 1×PBS. TRIzol reagent (1 mL vol.) was added directly to the flask and cells were lysed by pipette-mixing. The cell lysate was then recovered from the T25 flask and total RNA was isolated using standard methods. RNA concentrations were subsequently measured with a Nanodrop 2000 (Thermo Fisher). Strand cDNA was then generated from the isolated RNA according to the Takara PrimeScript II 1st strand cDNA synthesis kit protocol. Amplification of the hybridoma V-region of the resultant cDNA was then performed following Novagen user protocol TB326. Primer pairs, as shown in Table 3 below, were used for amplification:

TABLE 4

Primers for amplifying nucleic acids encoding anti-CD44 v7/8 antibodies

| | Primer | Sequence (5' to 3') |
|---|---|---|
| 1 | MuIgVH5'-A | GGGAATTCATGRASTTSKGGYTMARCTKGRTTT |
| 2 | MuIgVH5'-B | GGGAATTCATGRAATGSASCTGGGTYWTYCTCTT |
| 3 | MuIgVH5'-C1 | ACTAGTCGACATGGACTCCAGGCTCAATTTAGTTTTCCT |
| 4 | MuIgVH5'-C2 | ACTAGTCGACATGGCTGTCYTRGBGCTGYTCYTCTG |
| 5 | MuIgVH5'-C3 | ACTAGTCGACATGGVTTGGSTGTGGAMCTTGCYATTCCT |
| 6 | MuIgVH5'-D1 | ACTAGTCGACATGAAATGCAGCTGGRTYATSTTCTT |
| 7 | MuIgVH5'-D2 | ACTAGTCGACATGGRCAGRCTTACWTYYTCATTCCT |
| 8 | MuIgVH5'-D3 | ACTAGTCGACATGATGGTGTTAAGTCTTCTGTACCT |
| 9 | MuIgVH5'-E1 | ACTAGTCGACATGGGATGGAGCTRTATCATSYTCTT |
| 10 | MuIgVH5'-E2 | ACTAGTCGACATGAAGWTGTGGBTRAACTGGRT |
| 11 | MuIgVH5'-E3 | ACTAGTCGACATGGRATGGASCKKIRTCTTTMTCT |
| 12 | MuIgVH5'-F1 | ACTAGTCGACATGAACTTYGGGYTSAGMTTGRTTT |
| 13 | MuIgVH5'-F2 | ACTAGTCGACATGTACTTGGGACTGAGCTGTGTAT |
| 14 | MuIgVH5'-F3 | ACTAGTCGACATGAGAGTGCTGATTCTTTTGTG |
| 15 | MuIgVH5'-F4 | ACTAGTCGACATGGATTTTGGGCTGATTTTTTTATTG |
| 16 | MuIgMVH3'-1 | CCCAAGCTTACGAGGGGGAAGACATTTGGGAA |
| 17 | MuIgGVH3'-2 | CCCAAGCTTCCAGGGRCCARKGGATARACIGRTGG |
| 18 | MuIgkVL5'-A | GGGAATTCATGRAGWCACAKWCYCAGGTCTTT |
| 19 | MuIgkVL5'-B | GGGAATTCATGGAGACAGACACACTCCTGCTAT |
| 20 | MuIgkVL5'-C | ACTAGTCGACATGGAGWCAGACACACTSCTGYTATGGGT |
| 21 | MuIgkVL5'-D1 | ACTAGTCGACATGAGGRCCCCTGCTCAGWTTYTTGGIWTCTT |
| 22 | MuIgkVL5'-D2 | ACTAGTCGACATGGGCWTCAAGATGRAGTCACAKWYYCWGG |
| 23 | MuIgkVL5'-E1 | ACTAGTCGACATGAGTGTGCYCACTCAGGTCCTGGSGTT |
| 24 | MuIgkVL5'-E2 | ACTAGTCGACATGTGGGGAYCGKTTTYAMMCTTTTCAATTG |
| 25 | MuIgkVL5'-E3 | ACTAGTCGACATGGAAGCCCCAGCTCAGCTTCTCTTCC |

TABLE 4-continued

Primers for amplifying nucleic acids encoding anti-CD44 v7/8 antibodies

| | Primer | Sequence (5' to 3') |
|---|---|---|
| 26 | MuIgkVL5'-F1 | ACTAGTCGACATGAGIMMKTCIMTTCAITTCYTGGG |
| 27 | MuIgkVL5'-F2 | ACTAGTCGACATGAKGTHCYCIGCTCAGYTYCTIRG |
| 28 | MuIgkVL5'-F3 | ACTAGTCGACATGGTRTCCWCASCTCAGTTCCTTG |
| 29 | MuIgkVL5'-F4 | ACTAGTCGACATGTATATATGTTTGTTGTCTATTTCT |
| 30 | MuIgkVL5'-G1 | ACTAGTCGACATGAAGTTGCCTGTTAGGCTGTTGGTGCT |
| 31 | MuIgkVL5'-G2 | ACTAGTCGACATGGATTTWCARGTGCAGATTWTCAGCTT |
| 32 | MuIgkVL5'-G3 | ACTAGTCGACATGGTYCTYATVTCCTTGCTGTTCTGG |
| 33 | MuIgkVL5'-G4 | ACTAGTCGACATGGTYCTYATVTTRCTGCTGCTATGG |
| 34 | MuIgkVL3'-1 | CCCAAGCTTACTGGATGGTGGGAAGATGGA |
| 35 | MuIglVL5'-A | GGGAATTCATGGCCTGGAYTYCWCTYWTMYTCT |
| 36 | MuIglVL3'-1 | CCCAAGCTTAGCTCYTCWGWGGAIGGYGGRAA |

PCR products were checked with 1% Agarose gel. Positive PCR products were recovered using QIAgen gel extraction kits and subsequently cloned into pET28a vector using restriction enzymes (from NEB) corresponding to the primer sequence. pET28a vectors with PCR product insertion were transformed into DH5a bacterial cells and cultured on Ampicillin-positive agar plates. Each bacterial clone was sent for Sanger sequencing using the MuIgGVH3'-2, MuIgkVL3'-1 or MuIglVL3'-1 primers. Obtained sequences were compared for consistence to confirm target $V_H$ and $V_L$ sequences, respectively. $V_H$ and $V_L$ sequences were then analyzed on the IGMT database (imgt.org/) to provide the V-region, Frame and CDR elements of $V_H$ and $V_L$.

Example 2: In Vitro Evaluation of Anti-CD44 V7/8 Antibodies

Binding Activity to CD44 Variants

Peptide derived from CD44 v7 (PISHPMGRGHQAGRR; SEQ ID NO: 12), CD44 v7/8 (QAGRRMDMDSSHSIT; SEQ ID NO: 13), and CD44 v8 (SHSITLQPTANPNTG; SEQ ID NO: 14) were used to evaluate binding specificity of antibody clone HIS029.

Figure 1B:
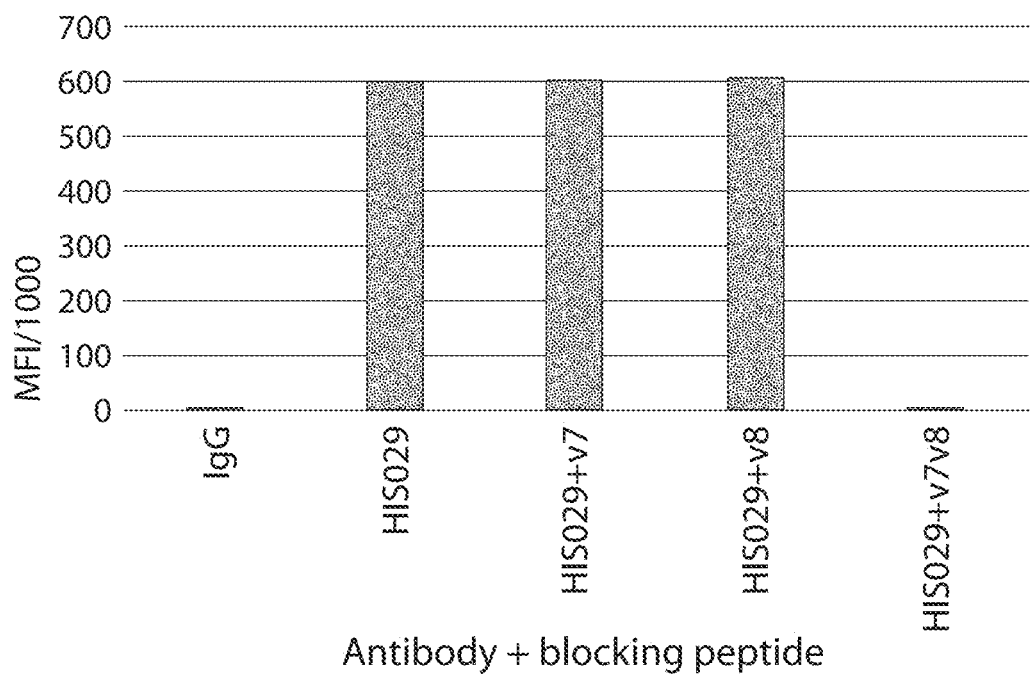

Samples of D526 cells were harvested using trypsin-EDTA partial digestion followed by centrifugation at 1000 rpm for 5 minutes. The cells were re-suspended in cold PBS and an anti-CD44 V7/8 antibody, HIS029, was added. The cell solutions were mixed, incubated at 4° C. in the dark and washed with PBS prior to addition of secondary antibody conjugates (for detection purposes). After incubation, the cells were washed with PBS before being mixed with one of the three CD44 peptides noted above. Following incubation of the D562/HIS029 samples with the CD44 peptides, samples were fixed with a fixative, and then subjected to flow cytometry (FACS) analysis. An IgG antibody incubated with D562 cells was used as a negative control. As shown in FIG. 1B, the anti-CD44 V7/8 antibody (HIS029) exhibited saturable binding to the CD44+ D562 cell sample in the absence of any peptide or in the presence of either the CD44 v7 or CD44 v8 peptides. Conversely, CD44 v7/8 peptide completely disrupted the binding interaction between HIS029 and D562 cells. These data suggest that anti-CD44 v7/8 antibodies as described herein target specifically CD44 v7/8.

Figure 2:
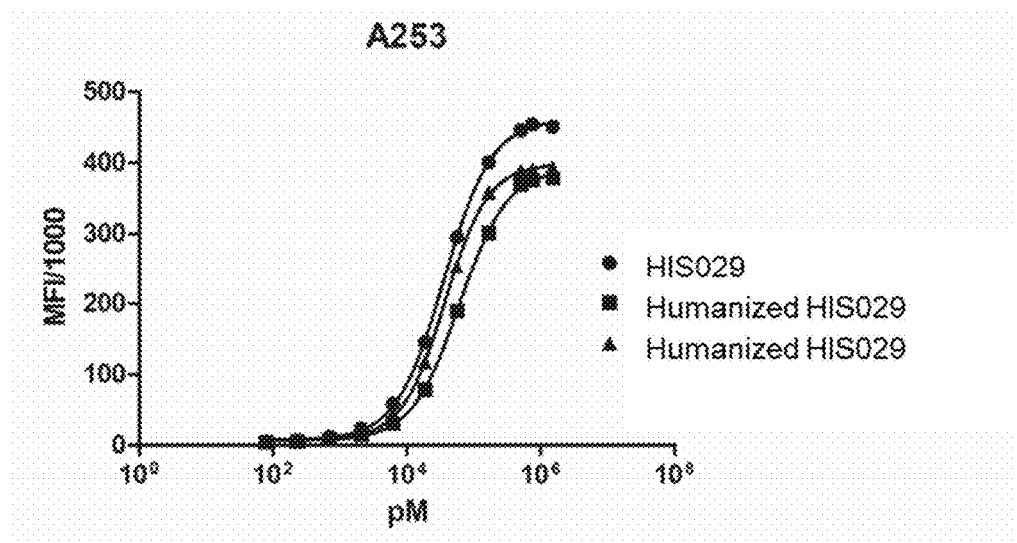
FIG. 2 is a diagram showing that anti-CD44 v7/8 antibodies (HIS029 and humanized HIS029) are capable of binding to A253 cells, which express CD44 v7/8 (CD44$^+$ cells).

Using the same FACS-based assay as above, it was further demonstrated that anti-CD44 v7/8 antibodies (HIS029 and humanized HIS029) bind to CD44+ A253 cells. HIS029 bound CD44+ A253 cells with a binding affinity of 35 nM; humanized HIS029 bound CD44+ A253 cells with a binding affinity of 36 nM (FIG. 2).

Example 3: Preparation and In Vitro Evaluation of Anti-CD44 v7/8 Antibody-Drug Conjugates An anti-CD44 v7/8 antibody-drug conjugate (ADC) comprising the HIS029 antibody and monomethyl auristatin E (HIS029-vc-MMAE) was generated. A linker molecule (maleimidocaproyl-L-valine-L-citrulline-p-aminobenzyl alcohol p-nitrophenyl carbonate) was first coupled to MMAE using an amide coupling reaction. After purification of this first compound, it was then coupled to HIS029 antibody using a thiol-based reaction.

Figure 3:
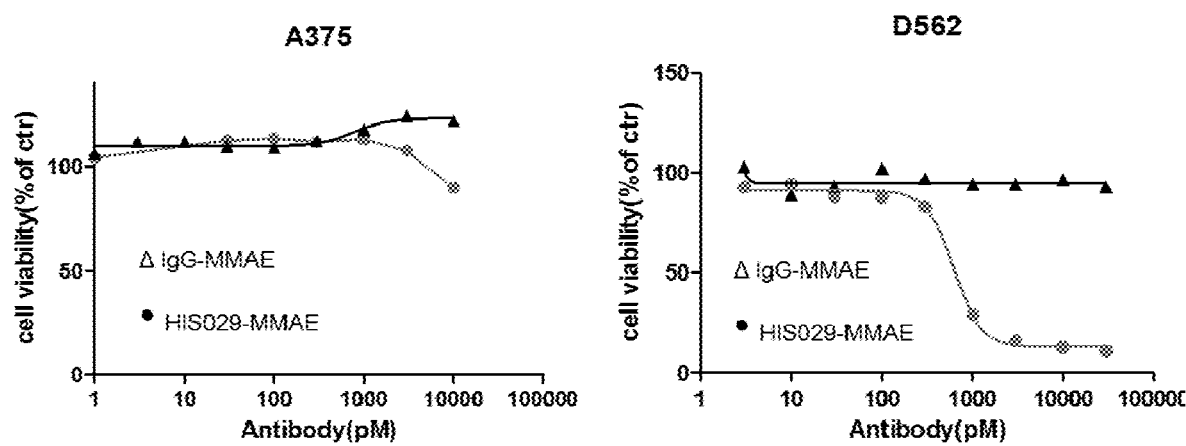
FIG. 3 includes diagrams showing that anti-CD44 v7/8 antibody-drug conjugate (HIS029 conjugated to MMAE using a Val-Cit linker (HIS029-MMAE)) is capable of specifically targeting a CD44$^+$ cancer cell lines. HIS029-MMAE demonstrates potent inhibition against CD44$^+$ Detroit 562 (D562) cells (right) and has limited inhibition against A375 cells.

HIS029-vc-MMAE was added to samples of CD44+ cells (A253, D562, NCI-H520, and BXPC3) to determine the ability of an anti-CD44 v7/8 ADC to be internalized into CD44+ cells and induce cytotoxicity. A375 cells, which have low expression levels of CD44, were utilized as a negative control cell line. All cell lines were dosed with either HIS029-vc-MMAE or a control ADC (IgG-vc-MMAE) at varying concentrations. After dosing, cell viability was assessed using standard methods. In the CD44+ D562 cell line, HIS029-vc-MMAE caused a decrease in cellular viability down to ~15% total viability, with $IC_{50}$ values of 630 pM, as shown in FIG. 3. In the control cell line (A375), HIS029-vc-MMAE caused a minimal decrease in cell viability at high concentrations of ADC; however with an undetermined $IC_{50}$ value. The IgG control antibody led to no significant losses in cellular viability. HIS029-vc-MMAE demonstrated a decrease in cell viability in the other CD44+ cell lines as well, with $IC_{50}$ values of 797 pM (A253), 588 pM (NCI-H520), and 189 pM (BXPC3) (data not shown).

Example 4: Preparation and In Vitro Evaluation of Anti-CD44 v7/8 CARP T Cells

Figure 4:
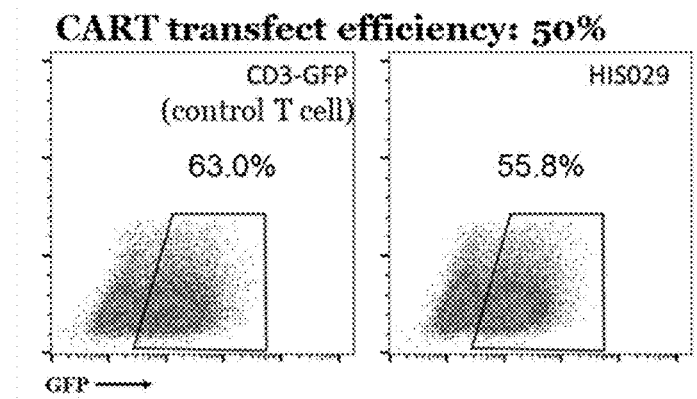
FIG. 4 includes figures showing transduction efficiency of anti-CD44 v7/8 CAR lentiviruses into CD3$^+$ T cells.

A humanized HIS029 antibody ($V_H$ and $V_L$) was inserted into a chimeric antigen receptor vector in frame with a CD8 hinge region, a CD8 transmembrane region, an intracellular domain of the co-stimulator 4-1BB, and an intracellular domain of CD3ζ. The vector further comprises an EF1α promotor. The nucleic acid encoding the anti-CD44 V7/8 CARP was transfected using lentiviral packaging into 293T cells. Human CD3+ T cells were then activated and transduced with lentivirus to produce anti-CD44 v7/8 CAR+ T cells. Following production of the anti-CD44 v7/8 CAR+ T cells as described above, the transduction efficiency for each CAR construct was determined using FACS (FIG. 4). T cell populations transduced with anti-CD44 v7/8 CARs comprised 55.8% CAR+ cells.

The ability of anti-CD44 v7/8 CAR+ T cells to induce antigen-dependent cytotoxicity and cytokine (IFNγ and IL2) secretion in CD44+ A253 cell line was tested. A549 cells, which have low expression levels of CD44, were utilized as a negative control cell line. Each cell line was dosed with anti-CD44 v7/8 CAR+ T cells or a control (CD3+ T cells) at varying ratios of T cells (Effector cells)-to-Target cells.

Figure 5A:
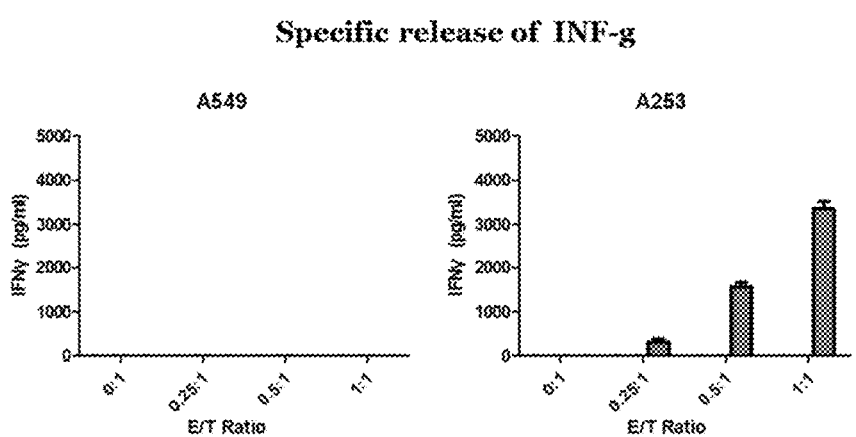
FIGS. 5A-5B include graphs showing the effect of CD44 v7/8 CAR$^+$ T cells in inducing secretion of cytokines when co-cultured with CD44$^+$ A523 cells and A549 cells (control cells).
Figure 5B:
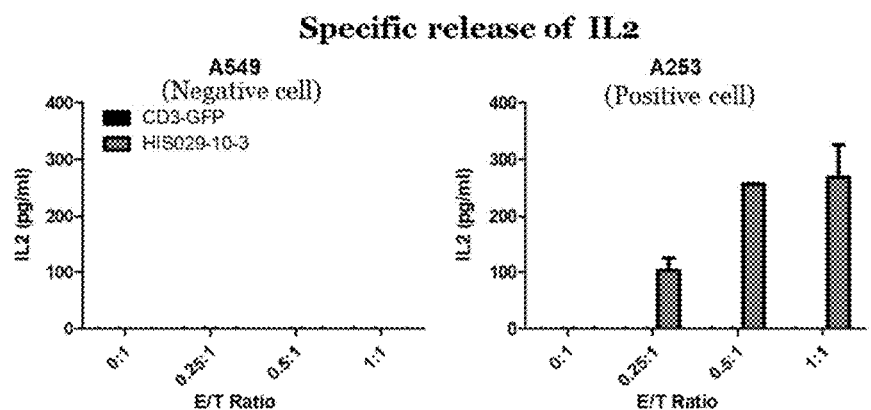
Figure 6:
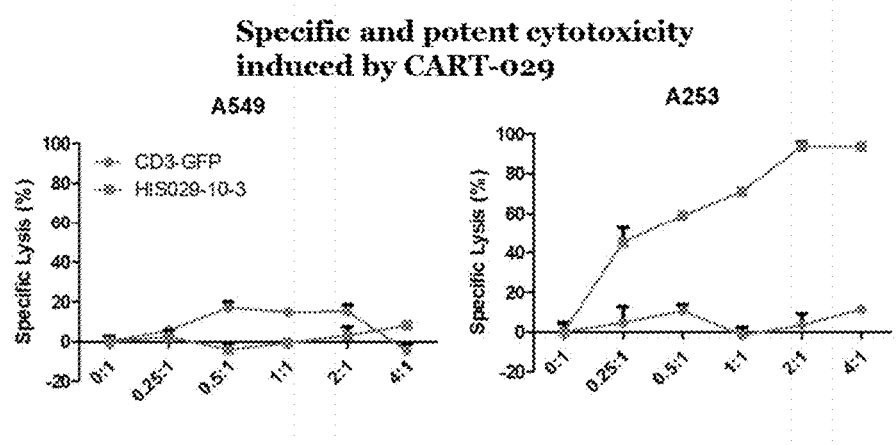
FIG. 6 includes graphs showing the effect of anti-CD44 v7/8 CAR$^+$ T cells in inducing antigen-dependent cytotoxicity against CD44$^+$ A523 cells and A549 cells (control cells). Anti-CD44 v7/8 CAR$^+$ T cells are effective in inducing antigen-dependent cytoxicity against CD44$^+$ A523 cells.

After incubation of the T cells with the target cells, specific lysis/cytotoxicity of the target cells were assessed using standard methods (FIGS. 5A, 5B, 6). In CD44+ A253 cells, the addition of anti-CD44 v7/8 CAR+ T cells induced antigen-dependent cytotoxicity at and above a ratio of 0.25:1 T cell:Target cell. The control experiments (incubation with CD3 T cells without a CAR; and A549 incubated with CAR+ T cells) led to no significant induction of specific cytotoxicity. The addition of anti-CD44 v7/8 CAR+ T cells induced levels of IFNγ and IL2 at and above a ratio of 0.25:1 T cell:Target cell. The control experiments (incubation with CD3 T cells without a CAR; and A549 incubated with CAR+ T cells) led to no significant secretion of IFNγ.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. An isolated antibody that binds to human CD44, wherein the antibody comprises a heavy chain variable region ($V_H$) comprising a heavy chain complementary determining region 1 (HC CDR1) of the amino acid sequence of SEQ ID NO: 2, a HC CDR2 of the amino acid sequence of SEQ ID NO: 3, and a HC CDR3 of the amino acid sequence of SEQ ID NO: 4, and a light chain variable region ($V_L$) comprising a light chain CDR1 (LC CDR1) of the amino acid sequence of SEQ ID NO: 5, a LC CDR2 of the amino acid sequence of SEQ ID NO: 6, and a LC CDR3 of the amino acid sequence of SEQ ID NO: 7.

2. The isolated antibody of claim 1, wherein the antibody does not bind peptide PISHPMGRGHQAGRR (SEQ ID NO: 12) or peptide SHSITLQPTANPNTG (SEQ ID NO: 14).

3. The isolated antibody of claim 1, wherein the $V_H$ of the isolated antibody is at least 85% identical to the amino acid sequence of SEQ ID NO: 10, and/or wherein the $V_L$ of the isolated antibody is at least 85% identical to the amino acid sequence of SEQ ID NO: 11.

4. The isolated antibody of claim 1, wherein the $V_H$ of the isolated antibody comprises the amino acid sequence of SEQ ID NO: 10, and/or wherein the $V_L$ of the isolated antibody comprises the amino acid sequence of SEQ ID NO: 11.

5. A nucleic acid or set of nucleic acids, which collectively encodes the isolated antibody of claim 1.

6. A vector or set of vectors comprising the nucleic acid(s) of claim 5.

7. A host cell comprising the vector or vector set of claim 6.

8. An antibody-drug conjugate (ADC) comprising: i. an antibody of claim 1; and ii. at least one therapeutic agent; wherein the antibody is covalently conjugated to the at least one therapeutic agent.

9. A pharmaceutical composition comprising (i) an antibody of claim 1, a nucleic acid or set of nucleic acids encoding the antibody, an antibody-drug conjugate comprising the antibody, or a host cell comprising the nucleic acid or set of nucleic acids encoding the antibody or a host cell which expresses a chimeric antigen receptor, comprising (a) an extracellular domain comprising an antigen binding fragment that specifically binds CD44 v7/8, (b) a transmembrane domain, and (c) one or more intracellular signaling domains; and (ii) a pharmaceutically acceptable carrier.

10. A method of inhibiting cells expressing CD44 v7/8, the method comprising administering to a subject in need thereof an effective amount of the pharmaceutical composition of claim 9.

11. A method of detecting presence of cells expressing surface CD44 v7/8, the method comprising: i. contacting a sample suspected of having cells expressing surface CD44 v7/8 with an antibody of claim 1, wherein the antibody is conjugated with a labeling agent; and ii. detecting presence cells expressing CD44 v7/8 in the sample based on binding of the antibody to cells in the sample.

12. The isolated antibody of claim 1, wherein the antibody is a full-length antibody or an antigen-binding fragment thereof, optionally wherein the full-length antibody is an IgG molecule.

13. The isolated antibody of claim 1, wherein the antibody is a single-chain antibody.

14. The isolated antibody of claim 1, wherein the antibody is a human antibody, a humanized antibody, or a chimeric antibody, optionally wherein the antibody comprises a $V_H$ set forth as SEQ ID NO: 8, and/or a $V_L$ set forth as SEQ ID NO: 9.

15. A chimeric antigen receptor, comprising: (i) an extracellular domain comprising an antigen binding fragment, (ii) a transmembrane domain, and (iii) one or more intracellular signaling domains, wherein the antigen binding fragment comprises a heavy chain variable region ($V_H$) comprising a heavy chain complementary determining region 1 (HC CDR1) of the amino acid sequence of SEQ ID NO: 2, a HC CDR2 of the amino acid sequence of SEQ ID NO: 3, and a HC CDR3 of the amino acid sequence of SEQ ID NO: 4, and a light chain variable region ($V_L$) comprising a light chain CDR1 (LC CDR1) of the amino acid sequence of SEQ ID NO: 5, a LC CDR2 of the amino acid sequence of SEQ ID NO: 6, and a LC CDR3 of the amino acid sequence of SEQ ID NO: 7.

16. The chimeric antigen receptor of claim 15, wherein the antigen binding fragment specifically binds an epitope of human CD44 v7/8, wherein the epitope comprises the amino acid sequence of QAGRRMDMDSSHSIT (SEQ ID NO: 13).

17. A nucleic acid, which comprises a nucleotide sequence encoding a chimeric antigen receptor of claim 15.

18. A vector comprising the nucleic acid of claim 17.

19. A host cell, which expresses a chimeric receptor of claim 15.

* * * * *

UNITED STATES PATENT AND TRADEMARK OFFICE
CERTIFICATE OF CORRECTION

PATENT NO. : 12,311,031 B2  
APPLICATION NO. : 17/386197  
DATED : May 27, 2025  
INVENTOR(S) : Shaofei Zhang et al.

Page 1 of 1

It is certified that error appears in the above-identified patent and that said Letters Patent is hereby corrected as shown below:

In the Specification

At Column 12, Lines 7-8:
"DIKMTQSFSSMYASLGERVTITCKASQDINRYLRWFQQKFGKSPKTLIYRANRLVDGVFSRFSGSGSGQDYSLTISSLEYEDMGIYYCLQYDEFPFTF"
Should read:
--DIKMTQSPSSMYASLGERVTITCKASQDINRYLRWFQQKPGKSPKTLIYRANRLVDGVPSRFSGSGSGQDYSLTISSLEYEDMGIYYCLQYDEFPFTF--

Signed and Sealed this
Twelfth Day of August, 2025

Coke Morgan Stewart
*Acting Director of the United States Patent and Trademark Office*

SEQUENCE LISTING

```
<160> NUMBER OF SEQ ID NOS: 14

<210> SEQ ID NO 1
<211> LENGTH: 742
<212> TYPE: PRT
<213> ORGANISM: Homo sapiens

<400> SEQUENCE: 1

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
    210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
            260                 265                 270

Ser Ala Gly Trp Glu Pro Asn Glu Glu Asn Glu Asp Glu Arg Asp Arg
        275                 280                 285

His Leu Ser Phe Ser Gly Ser Gly Ile Asp Asp Asp Glu Asp Phe Ile
    290                 295                 300
```

```
Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
            325                 330                 335

Leu Leu Gln Thr Thr Thr Arg Met Thr Asp Val Asp Arg Asn Gly Thr
                340                 345                 350

Thr Ala Tyr Glu Gly Asn Trp Asn Pro Glu Ala His Pro Pro Leu Ile
        355                 360                 365

His His Glu His His Glu Glu Glu Thr Pro His Ser Thr Ser Thr
    370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ala Ser Ala His
            420                 425                 430

Thr Ser His Pro Met Gln Gly Arg Thr Thr Pro Ser Pro Glu Asp Ser
        435                 440                 445

Ser Trp Thr Asp Phe Phe Asn Pro Ile Ser His Pro Met Gly Arg Gly
450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
                500                 505                 510

Phe Ser Thr Ser His Glu Gly Leu Glu Glu Asp Lys Asp His Pro Thr
            515                 520                 525

Thr Ser Thr Leu Thr Ser Ser Asn Arg Asn Asp Val Thr Gly Gly Arg
            530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
            595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
            675                 680                 685

Gly Ala Val Glu Asp Arg Lys Pro Ser Gly Leu Asn Gly Glu Ala Ser
            690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
```

Asp Met Lys Ile Gly Val
            740

<210> SEQ ID NO 2
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 2

Gly Tyr Thr Phe Thr Asn Tyr Trp
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 3

Ile Tyr Pro Ser Asp Ser Tyr Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 4

Thr Lys Trp Gly Asp Ser Asp Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 5

Gln Asp Ile Asn Arg Tyr
1               5

<210> SEQ ID NO 6
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 6

Arg Ala Asn
1

<210> SEQ ID NO 7
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 7

```
Leu Gln Tyr Asp Glu Phe Pro Phe Thr
1               5
```

```
<210> SEQ ID NO 8
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 8
```

```
Gln Val His Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Asn Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Thr Ala Tyr
65                  70                  75                  80

Val His Leu Ser Ser Pro Thr Ser Glu Asp Ser Ala Val Tyr Tyr Cys
                85                  90                  95

Thr Lys Trp Gly Asp Ser Asp Tyr Trp Gly Gln Gly Thr Thr Leu Thr
            100                 105                 110

Val Ser Ser
        115
```

```
<210> SEQ ID NO 9
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 9
```

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Arg Tyr
            20                  25                  30

Leu Arg Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Phe
                85                  90                  95

Thr Phe Gly Ser Gly Thr Lys Leu Glu Ile Lys
            100                 105
```

```
<210> SEQ ID NO 10
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 10
```

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Pro Gly Gln Gly Leu Glu Trp Met
            35                  40                  45

Gly Asn Ile Tyr Pro Ser Asp Ser Tyr Thr Asn Tyr Asn Gln Lys Phe
        50                  55                  60

Lys Asp Arg Ala Val Phe Ser Val Asp Lys Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Lys Trp Gly Asp Ser Asp Tyr Trp Gly Gln Gly Thr Thr Val Thr
            100                 105                 110

Val Ser Ser
        115

<210> SEQ ID NO 11
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Arg Tyr
            20                  25                  30

Leu Arg Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Phe
                85                  90                  95

Thr Phe Gly Gln Gly Thr Lys Leu Glu Ile Lys
            100                 105

<210> SEQ ID NO 12
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 12

Pro Ile Ser His Pro Met Gly Arg Gly His Gln Ala Gly Arg Arg
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 13

Gln Ala Gly Arg Arg Met Asp Met Asp Ser Ser His Ser Ile Thr

```
1               5               10              15

<210> SEQ ID NO 14
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 14

Ser His Ser Ile Thr Leu Gln Pro Thr Ala Asn Pro Asn Thr Gly
1               5                   10                  15
```